United States Patent
Kiyono (10) Patent No.: US 7,245,691 B2
(45) Date of Patent: Jul. 17, 2007

(54) RADIATION TOMOGRAPHIC IMAGING APPARATUS AND IMAGING METHOD USING IT

(75) Inventor: Satoshi Kiyono, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/030,226

(22) Filed: Jan. 6, 2005

(65) Prior Publication Data

US 2005/0147198 A1    Jul. 7, 2005

(30) Foreign Application Priority Data

Jan. 7, 2004   (JP)   .............. 2004-002125

(51) Int. Cl.
*G21K 1/12*   (2006.01)
(52) U.S. Cl. ........................... 378/4; 378/901
(58) Field of Classification Search ............ 378/4, 378/8, 20, 21, 9, 210, 901
See application file for complete search history.

(56) References Cited

U.S. PATENT DOCUMENTS

| | | | |
|---|---|---|---|
| 4,135,247 A * | 1/1979 | Gordon et al. | 378/11 |
| 4,219,879 A | 8/1980 | Mizutani et al. | 708/3 |
| 4,245,244 A * | 1/1981 | Lijewski et al. | 378/98.5 |
| 4,649,555 A * | 3/1987 | Matsubayashi | 378/4 |
| 5,412,702 A * | 5/1995 | Sata | 378/4 |
| 5,612,985 A | 3/1997 | Toki et al. | 378/4 |
| 5,627,868 A * | 5/1997 | Nobuta et al. | 378/19 |
| 6,424,692 B1 * | 7/2002 | Suzuki | 378/4 |
| 6,801,594 B1 | 10/2004 | Ali et al. | 378/4 |
| 2003/0123603 A1 * | 7/2003 | Suzuki | 378/4 |

FOREIGN PATENT DOCUMENTS

JP   2001-190538   7/2001

* cited by examiner

*Primary Examiner*—Courtney Thomas
*Assistant Examiner*—Alexander Taningco
(74) *Attorney, Agent, or Firm*—Carl B. Horton, Esq.; Armstrong Teasdale LLP (57) ABSTRACT

A radiation tomographic imaging apparatus includes a scanning device for scanning a predefined region in a subject, a prescribing device for prescribing beforehand a position at which an image of said subject is to be produced at a higher priority in the scan region in said subject and a reconstructing device for sequentially reconstructing an image of said subject from projection data obtained by said scanning device, wherein once projection data at said prescribed higher-priority position has been obtained from said scanning device, said reconstructing device reconstructs an image at said higher-priority position at a higher priority.

18 Claims, 4 Drawing Sheets

RADIATION TOMOGRAPHIC IMAGING APPARATUS AND IMAGING METHOD USING IT

CROSS REFERENCE TO RELATED APPLICATIONS

This application claims the benefit of Japanese Application No. 2004-002125 filed Jan. 7, 2004.

BACKGROUND OF THE INVENTION

The present invention relates to a radiation tomographic imaging apparatus and an imaging method, and more particularly to a radiation tomographic imaging apparatus and an imaging method for producing a tomographic image at a predefined position in a subject during a scan.

As an apparatus for capturing a tomographic image, there is known, for example, an X-ray CT (computed tomography) apparatus for emitting X-rays as radiation, detecting X-rays passing through a subject, and arithmetically producing a tomographic image.

The X-ray CT apparatus has a scan gantry comprised of an X-ray tube and a detector array disposed to face the X-ray tube with the subject placed therebetween, and detects X-rays emitted toward the subject from the X-ray tube by the detector array. The X-ray CT apparatus scans the subject placed on an imaging table while, for example, rotating the scan gantry around the subject. Consequently, projection data of the subject are obtained in a plurality of views. The X-ray CT apparatus reconstructs the resulting projection data to produce a tomographic image of the subject of a predetermined slice thickness.

In such an X-ray CT apparatus, there is known a method of producing an image by sequentially performing reconstruction on projection data obtained in a scan (for example, see Patent Document 1). The method displays the reconstructed image on a display device or the like in the order of the image production, for example. If the speed of reconstruction is slow relative to that of scanning, the position being scanned does not coincide with the position of the image being reconstructed and displayed.

There is a method of performing reconstruction at a scan position selected by a user at a higher priority. In the case of such a method, the X-ray CT apparatus interrupts current reconstruction processing upon the selection of a certain position by a user during a scan by the scan gantry, and uses the latest projection data at the time of the selection to perform reconstruction. However, since the X-ray CT apparatus interrupts reconstruction processing to perform reconstruction at the certain position only after the user has selected a scan position, there is a lag between the selection of the position by the user and the display of a desired image by the X-ray CT apparatus.

Moreover, to select a certain position in this method, the user confirms a display indicating a scan time or a scan position, and visually identifies a position in the subject. It is difficult, however, for the method to provide accurate position information. Consequently, even if the user selects a scan position with such a method, a reconstructed image may be offset from the expected position.

[Patent Document 1] Japanese Patent Application Laid Open No. 2001-190538.

SUMMARY OF THE INVENTION

Therefore, an object of the present invention is to provide a radiation tomographic imaging apparatus and an imaging method using it that, in simultaneously conducting a scan and image reconstruction, can reduce lag of the speed of reconstruction relative to the scan, and enables confirmation of a tomographic image at a desired position.

To attain the aforementioned object, a radiation tomographic imaging apparatus of the present invention comprise: scanning means for scanning a predefined region in a subject; prescribing means for prescribing beforehand a position at which an image of the subject is to be produced at a higher priority in the scan region in the subject; and reconstructing means for sequentially reconstructing an image of the subject from projection data obtained by the scanning means. Once projection data at the prescribed higher-priority position has been obtained from the scanning means, the reconstructing means reconstructs an image at the higher-priority position at a higher priority.

According to the radiation tomographic imaging apparatus of the present invention, an image production position at which reconstruction is to be made at a higher priority is prescribed beforehand. Once the prescribed higher-priority position has been scanned, the image is reconstructed at a higher priority than that for previously obtained projection data.

To attain the aforementioned object, a radiation tomographic imaging apparatus of the present invention comprises: scanning means for consecutively scanning a predefined position in a subject; prescribing means for prescribing beforehand a time at which obtained projection data is to be reconstructed at a higher priority at the scan position in the subject; and reconstructing means for sequentially reconstructing an image of the subject from projection data obtained by the scanning means. Once projection data at the prescribed higher-priority time has been obtained from the scanning means, the reconstructing means reconstructs an image of the subject at the higher-priority time at a higher priority.

According to the radiation tomographic imaging apparatus of the present invention, a scan time at which reconstruction is to be made at a higher priority is prescribed beforehand. Moreover, once projection data at the prescribed scan time has been obtained, the image is reconstructed at a higher priority than that for previously obtained projection data.

To attain the aforementioned object, an imaging method of the present invention uses a radiation tomographic imaging apparatus having a radiation source and a radiation detector disposed to face the radiation source with a subject placed therebetween, and comprises the steps of: defining a reference position in the subject placed at a certain position; prescribing an image production position in the subject at which reconstruction is to be made at a higher priority, based on the reference position; scanning a predefined region in the subject placed at the certain position while rotating at least one of the radiation source and radiation detector around the subject; and sequentially reconstructing an image at every image production position based on the projection data obtained at the step of scanning. The step of scanning and step of reconstructing run simultaneously, and once projection data at the higher-priority position has been obtained at the step of scanning, the step of reconstructing reconstructs an image at the higher-priority position at a higher priority.

According to the imaging method of the present invention, a reference position is defined in a subject placed at a certain position. Based on the reference position, an image production position in the subject at which reconstruction is to be made at a higher priority is prescribed. A predefined region in the subject placed at the certain position is then scanned while rotating the radiation source and radiation detector around the subject. Next, an image at every image production position is sequentially reconstructed based on the projection data obtained by the scan. The scanning and reconstruction processing run simultaneously, and once projection data at the higher-priority position has been obtained by the scan, the reconstruction processing reconstructs an image at the higher-priority position at a higher priority.

To attain the aforementioned object, an imaging method of the present invention uses a radiation tomographic imaging apparatus having a radiation source and a radiation detector disposed to face the radiation source with a subject placed therebetween, and comprises the steps of: defining a reference position in the subject placed at a certain position; prescribing a time from the beginning of a scan at which reconstruction is to be made at a higher priority; consecutively scanning a predefined position in the subject based on the reference position while rotating at least one of the radiation source and radiation detector around the subject; and sequentially reconstructing an image at an image production position based on the projection data obtained at the step of scanning. The step of scanning and step of reconstructing run simultaneously, and once projection data at the higher-priority time has been obtained at the step of scanning, the step of reconstructing reconstructs an image of the subject at the higher-priority time at a higher priority.

According to the imaging method of the present invention, a reference position is defined in a subject placed at a certain position. Then, a time from the beginning of scanning at which reconstruction is to be made at a higher priority is prescribed. Next, a predefined position in the subject is consecutively scanned based on the reference position while relatively rotating the radiation source and radiation detector around the subject. Based on the projection data obtained by the scan, an image at an image production position is sequentially reconstructed. The scanning and reconstruction processing run simultaneously. Moreover, once projection data at the higher-priority time has been obtained by the scan, the reconstruction processing reconstructs an image of the subject at a higher-priority time at a higher priority.

According to the radiation tomographic imaging apparatus of the present invention, in simultaneously conducting a scan and image reconstruction, lag of the speed of reconstruction relative to the scan is reduced, and confirmation can be made on a tomographic image at a desired position. Moreover, according to the imaging method of the present invention, in simultaneously conducting a scan and image reconstruction, lag of the speed of reconstruction relative to the scan is reduced, and confirmation can be made on a tomographic image at a desired position. Further objects and advantages of the present invention will be apparent from the following description of the preferred embodiments of the invention as illustrated in the accompanying drawings.

DETAILED DESCRIPTION OF THE INVENTION

The best mode for carrying out the present invention will be now described with reference to the accompanying drawings.

Figure 1:
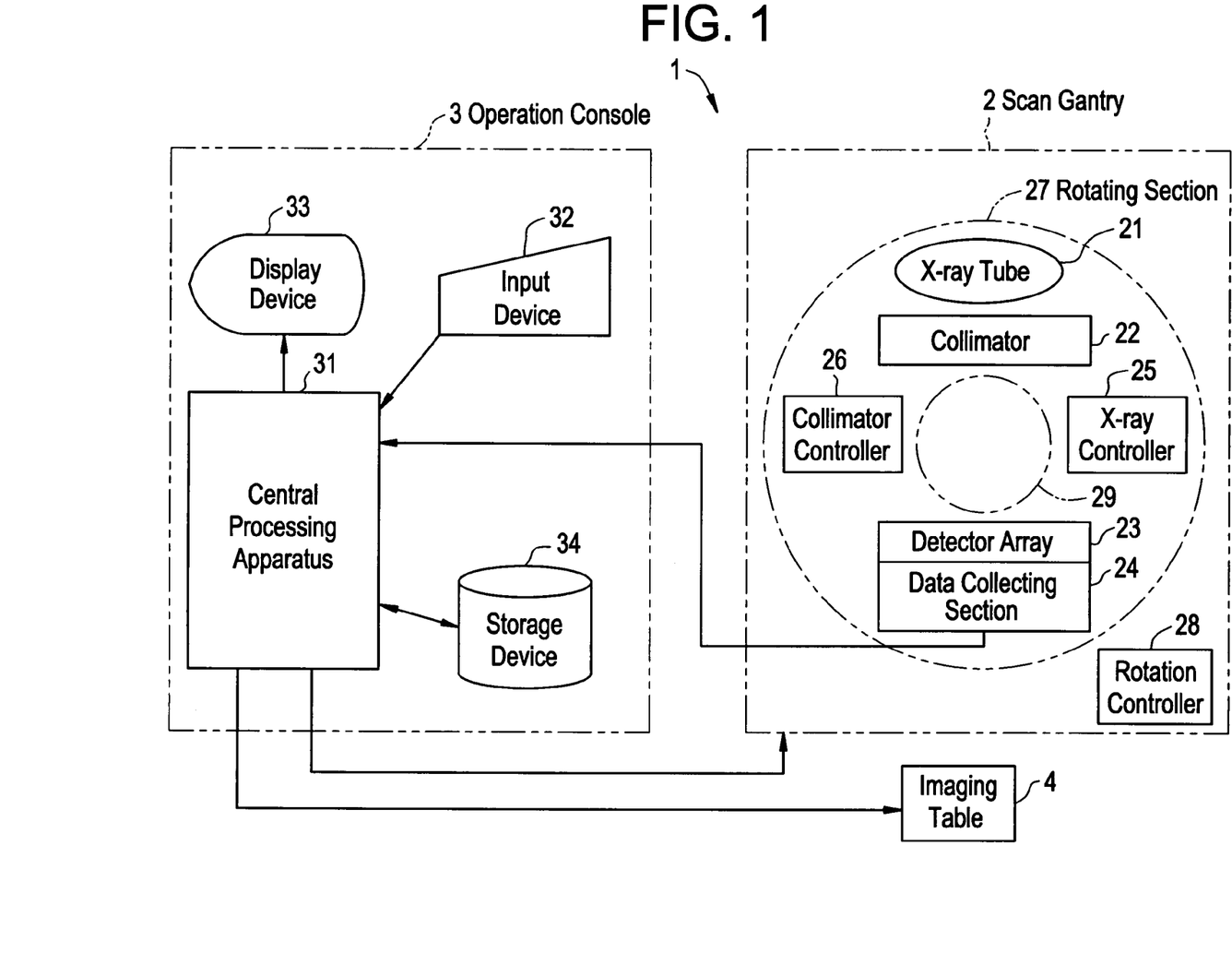
FIG. 1 is a block diagram schematically showing an X-ray CT apparatus 1 in accordance with one embodiment of the present invention.

FIG. 1 is a block diagram showing the overall configuration of an X-ray CT apparatus 1 in accordance with an embodiment of the present invention. One embodiment of the radiation tomographic imaging apparatus of the present invention is represented by the X-ray CT apparatus 1 employing X-rays as radiation.

As shown in FIG. 1, the X-ray CT apparatus 1 comprises a scan gantry 2, an operation console 3, and an imaging table (cradle) 4. The imaging table 4 has a subject placed thereon at a certain position.

The scan gantry 2 comprises an X-ray tube 21, a collimator 22, a detector array 23, a data collecting section 24, an X-ray controller 25, and a collimator controller 26. One embodiment of the scanning means of the present invention is represented by the scan gantry 2. The X-ray tube 21 emits X-rays. The X-rays emitted by the X-ray tube 21 are shaped by the collimator 22, and cast upon the detector array 23. One embodiment of the radiation source of the present invention is represented by the X-ray tube 21.

The detector array 23 is, for example, a multi-row detector comprising a plurality of X-ray detector elements arranged in a two-dimensional manner. The detector array 23 detects X-rays passing through the subject. One embodiment of the radiation detector of the present invention is represented by the detector array 23. The detector array 23 generally forms a semicircular-cylindrically concaved X-ray reception surface. The detector array 23 is made of a combination of scintillators and photodiodes, for example. The X-ray detector array 23 is, however, not limited to having such a configuration but may comprise, for example, semiconductor X-ray detector elements employing a cadmium-tellurium (CdTe) or ionization chamber X-ray detector elements employing Xe gas. The detector array 23 is connected to the data collecting section 24.

The data collecting section 24 collects data detected by the individual X-ray detector elements in the detector array 23. The X-ray controller 25 controls emission of X-rays from the X-ray tube 21. The collimator controller 26 controls the collimator 22. The interconnection between the X-ray tube 21 and X-ray controller 25, and that between the collimator 22 and collimator controller 26 are omitted in the drawing.

The X-ray tube 21, collimator 22, detector array 23, data collecting section 24, X-ray controller 25 and collimator controller 26 are mounted on a rotating section 27 of the scan gantry 2. The subject is placed on the imaging table 4 in a bore 29 in the center of the rotating section 27.

The rotating section 27 rotates under control by a rotation controller 28. The rotating section 27 emits X-rays at the X-ray tube 21, and detects X-rays passing through the subject at the detector array 23 as projection information for each view. The interconnection between the rotating section 27 and rotation controller 28 is omitted in the drawing.

The operation console 3 comprises a central processing apparatus 31, an input device 32, a display device 33, and a storage device 34.

The central processing apparatus 31 is comprised of a CPU, a program and a memory, for example. The central processing apparatus 31 controls the operation of the scan gantry 2 in accordance with a program stored in the storage device 34, which will be discussed later. The central processing apparatus 31 also has at least a function of collecting projection data obtained by the detector array 23, and a function of reconstructing a tomographic image of the subject based on the collected projection data. The central processing apparatus 31 will be discussed in detail later. The central processing apparatus 31 is connected with the scan gantry 2, imaging table 4, display device 33, input device 32, and storage device 34.

The display device 33 displays tomographic image information and the like output from the central processing apparatus 31. One embodiment of the display means of the present invention is represented by the display device 33. The input device 32 is operated by a user, and supplies several kinds of commands and information to the central processing apparatus 31. The user uses the display device 33 and input device 32 to interactively operate the present apparatus. The storage device 34 is comprised of a program, a memory and the like. The storage device 34 stores projection data, tomographic image information and the like output from the central processing apparatus 31.

Figure 2:
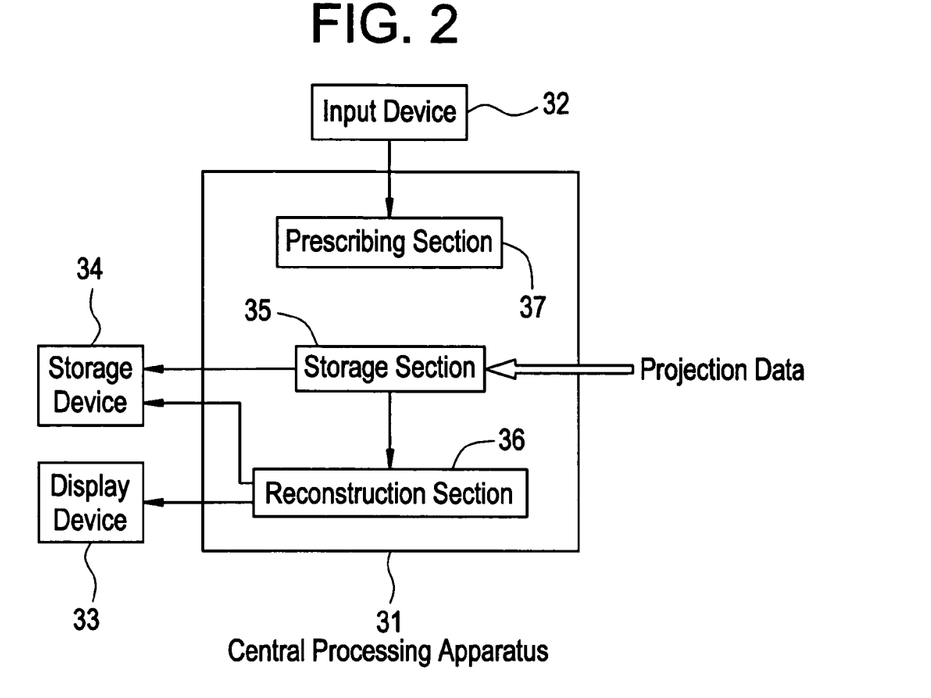
FIG. 2 is a block diagram schematically showing the configuration of the central processing apparatus 31 shown in FIG. 1.

FIG. 2 is a block diagram showing an exemplary configuration of the central processing apparatus 31.

As shown in FIG. 2, the central processing apparatus 31 comprises a storage section 35, a reconstruction section 36, and a prescribing section 37, for example. The storage section 35 temporarily stores projection data output from the data collecting section 24 to the central processing apparatus 31. The storage section 35 also outputs the projection data to the reconstruction section 36 and storage device 34. The reconstruction section 36 produces a tomographic image of the subject during a scan using the projection data output from the storage section 35. The reconstruction section 36 may produce a tomographic image of the subject after all scans are completed using projection data stored in the storage section 35 and performing interpolation on the data. The reconstruction section 36 outputs the produced image to the display device 33 and storage device 34. One embodiment of the reconstructing means of the present invention is represented by the reconstruction section 36. The prescribing section 37 prescribes beforehand a scan position at which reconstruction is to be made at a higher priority via the input device 32 or display device 33. One embodiment of the prescribing means of the present invention is represented by the prescribing section 37.

Now the operation of the X-ray CT apparatus 1 in accordance with the present invention will be described with reference to the drawings.

Figure 3:
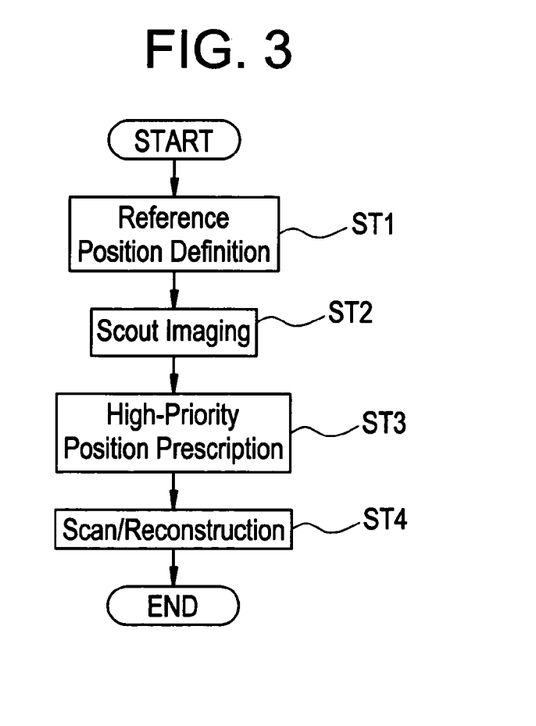
FIG. 3 is a flow chart showing an exemplary operation of the X-ray CT apparatus 1 shown in FIG. 1.

FIG. 3 is a flow chart showing an exemplary operation of the X-ray CT apparatus 1 of the present invention. The imaging method of the present invention is implemented using the X-ray CT apparatus 1 of the present invention.

The user first defines a reference position in a subject placed on the imaging table 4 (ST1).

The user positions the scan gantry 2 and imaging table 4 at a certain distance therebetween. Then, with the subject placed on the imaging table 4, the central processing apparatus 31 defines the positional relationship between the scan gantry 2 and subject as a reference position. The storage device 34 stores the defined reference position. This step corresponds to the step of defining a reference position of the present invention.

The user next specifies a direction and a region for scout imaging via the input device 32, and scout imaging is conducted based on the defined range (ST2).

The scan gantry 2 and imaging table 4 are controlled by the central processing apparatus 31 to scan the subject in the defined range and direction based on the specified conditions. At that time, the scan gantry 2 conducts the scan while translating and without rotating, with the X-ray tube 21 and detector array 23 kept at a constant position. The detector array 23 outputs the resulting projection data to the central processing apparatus 31 via the data collecting section 24. The central processing apparatus 31 produces a scout image based on the projection data, and outputs the image to the display device 33. The scout imaging may be omitted as needed. If the reference position is defined at Step ST1, it is possible to define a scan range, an image production spacing and the like as will be described below. In this case, a scout image cannot be used as a reference to define these settings.

The user next views the scout image of the subject displayed on the display device 33, and conducts settings such as scan conditions, reconstruction conditions, and a higher-priority position at which reconstruction is to be made at a higher priority (ST3).

The user uses the input device 32 to input a scan range defined by the distance from the reference position in the subject, an image production spacing, a slice thickness and the like with reference to the scout image displayed on the display device 33, for example. At the same time, the user also specifies an effective field of view (which will be referred to as FOV hereinbelow), a window width (which will be referred to as W/W hereinbelow), a window level (which will be referred to as W/L hereinbelow), and other reconstruction conditions. The central processing apparatus 31 outputs the imaging conditions and reconstruction conditions input by the user to the storage device 34. The storage device 34 stores the imaging conditions and reconstruction conditions. The central processing apparatus 31 also outputs the imaging conditions input by the user to the display device 33. The display device 33 superimposes on the scout image a scan start position, a scan end position, and an image production spacing, i.e., image production positions.

Figure 4:
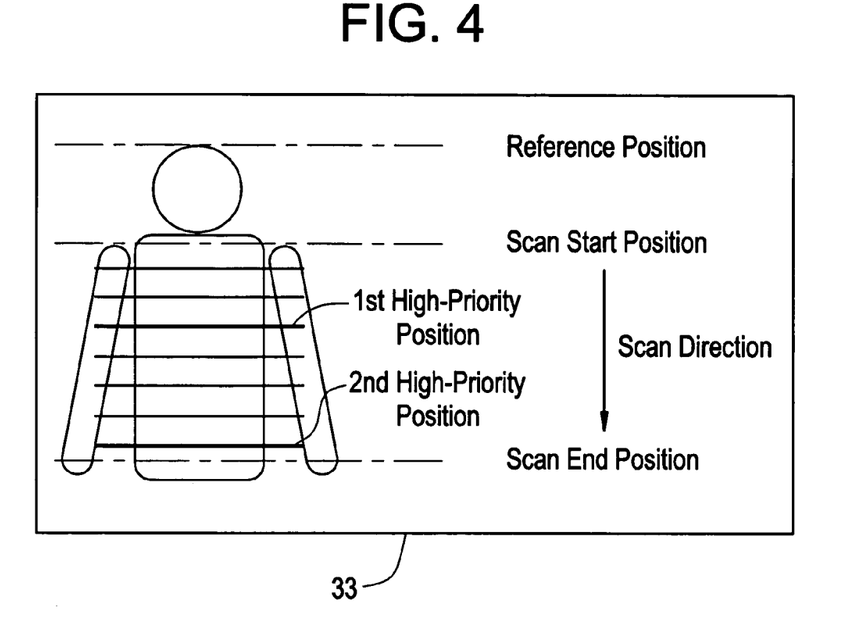
FIG. 4 is a schematic diagram showing an exemplary scout image displayed on the display device 33 shown in FIG. 1.

FIG. 4 is a schematic diagram generally showing an exemplary scout image and imaging conditions displayed on the display device 33.

As shown in FIG. 4, image production positions are displayed on a scout image of the subject corresponding to the distance from the reference position. The user views the display shown in FIG. 4 and selects a position at which reconstruction is to be made at a higher priority from the displayed image production positions. For example, the user uses a cursor or the like on the display device 33 to select a position near the region of interest as a first higher-priority position, and the last image production position in the scan direction as a second higher-priority position. Alternatively, the user may directly specify position information such as a numeric value corresponding to the distance from the reference position, for example, via the input device 32 and the like. The prescribing section 37 in the central processing apparatus 31 prescribes the image production positions selected on the display device 33 as higher-priority positions. The central processing apparatus 31 controls the storage device 35 and reconstruction section 36 based on the conditions prescribed in the prescribing section 37. The higher-priority position is defined for, for example, confirming imaging of a region of interest or in a scan range. Consequently, the user can obtain a desired reconstructed image at a higher-priority position not being offset from an expected position. This step corresponds to the step of prescribing a higher-priority position of the present invention.

Next, a scan is conducted on the subject based on the scan conditions input by the user, and reconstruction is sequentially performed based on projection data obtained by the scan (ST4).

The scan gantry 2 scans the subject based on the scan conditions specified at Step ST3 under control of the central processing apparatus 31. At that time, the scan gantry 2 outputs, for example, a distance between the reference position and rotating detector array 23, to the central processing apparatus 31. The data collecting section 24 in the scan gantry 2 outputs the detected projection data to the storage section 35 in the central processing apparatus 31. This step corresponds to the step of scanning of the present invention.

On the other hand, the central processing apparatus 31 causes the projection data corresponding to each image production position stored in the storage section 35 to be output to the reconstruction section 36. The reconstruction section 36 reconstructs an image from projection data at each image production position output from the storage section 35. The central processing apparatus 31 outputs the reconstructed images to the display device 33.

When the scan gantry 2 comes close to the first higher-priority position prescribed near the region of interest, the central processing apparatus 31 stops the outputting of projection data from the storage section 35 to the reconstruction section 36. The storage section 35 also outputs the stored projection data to the storage device 34. Moreover, the reconstruction section 36 interrupts reconstruction processing, and outputs data at the interruption to the storage device 34. The reconstruction section 36 is brought to a state in which it has no data to be reconstructed, i.e., to a reset state.

The central processing section 31 then outputs projection data obtained by the scan gantry 2 scanning a region corresponding to the higher-priority position to the reconstruction section 36 via the storage section 35. As a result, the reconstruction section 36 performs reconstruction processing upon inputting of projection data without a lag. The reconstruction section 36 can thus reconstruct an image at a higher-priority position at a higher priority, and the user can confirm whether an image at a desired position has been obtained. This step corresponds to the reconstructing step of the present invention.

At that time, the scan gantry 2 scans the scan region simultaneously with the reconstruction processing. Subsequently, the storage section 35 in the central processing apparatus 31 restarts storing of projection data from that corresponding to an image at a position subsequent to the higher-priority position in the scan direction. The reconstruction section 36 restarts reconstruction of an image at an image production position from the projection data output from the storage section 35. The central processing apparatus 31 sequentially outputs the reconstructed image to the display device 33. The reconstruction may be restarted from the image production position at which reconstruction is interrupted or from an arbitrary position selected by the user, depending upon the speed of execution of reconstruction processing at the reconstruction section 36.

Figure 5:
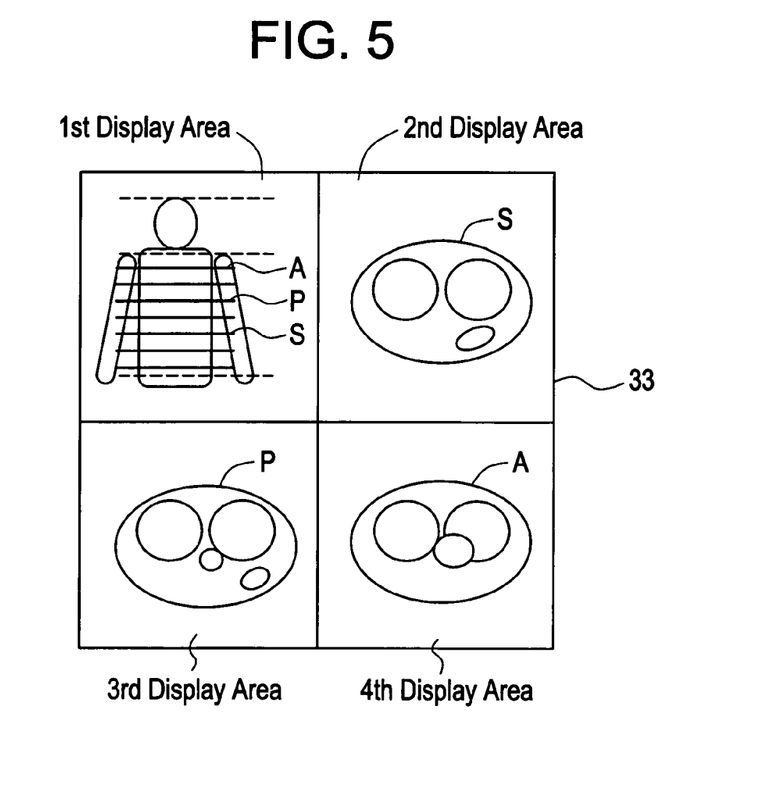
FIG. 5 is a schematic diagram showing an exemplary image displayed on the display device 33 shown in FIG. 1.

FIG. 5 is a schematic diagram showing an exemplary display on the display device 33 during a scan.

As shown in FIG. 5, the display device 33 is divided into a plurality of display sections, and displays different images in the sections. For example, the first display section displays a scout image indicating image production positions and a scan region, and the second display section displays the latest reconstructed image at the time of display. The third display section displays a reconstructed image at a higher-priority position, i.e., an image reconstructed at a higher priority. The fourth display section displays a reconstructed image at the image production position closest to the scan start position.

In this case, the reconstructed image at the higher-priority position displayed in the third display section is displayed until all scans are completed. Alternatively, it may be displayed until all reconstructions are completed.

Similarly, at the higher-priority position defined at the scan end position, the reconstruction section 36 in the central processing apparatus 31 interrupts other reconstruction processing, and produces an image from projection data output from the scan gantry 2. The display device 33 displays the produced image on the third display section. This step corresponds to the displaying step of the present invention.

When the scan gantry 2 has completed the scan over the scan range defined at Step ST3, the central processing apparatus 31 may conduct further image reconstruction at the specified image production positions based on the projection data stored in the storage device 34 while interpolating the data.

<<Variation 1>>

At Step ST3, instead of defining a certain region, it is possible to define a scan position, inject a contrast agent into the subject, and consecutively scan the same position, for example. In this case, the user specifies a scan position, a scan time and reconstruction conditions. The user also specifies, for example, an image production interval and an image to be reconstructed at a higher priority, using a time from the scan start and the like.

Based on the specified scan position and scan time, the central processing apparatus 31 performs reconstruction based on the projection data obtained by the scan gantry 2, as in Step ST4. Since the user can specify a higher-priority time at which reconstruction is to be made at a higher priority beforehand as described above, a desired image can be obtained in imaging using a contrast agent to observe a temporal process, for example. The higher-priority time specified may be a certain continuous time period. As a result, the central processing apparatus 31 reconstructs a plurality of images based on projection data obtained within the specified time period.

<<Variation 2>>

Figure 6:
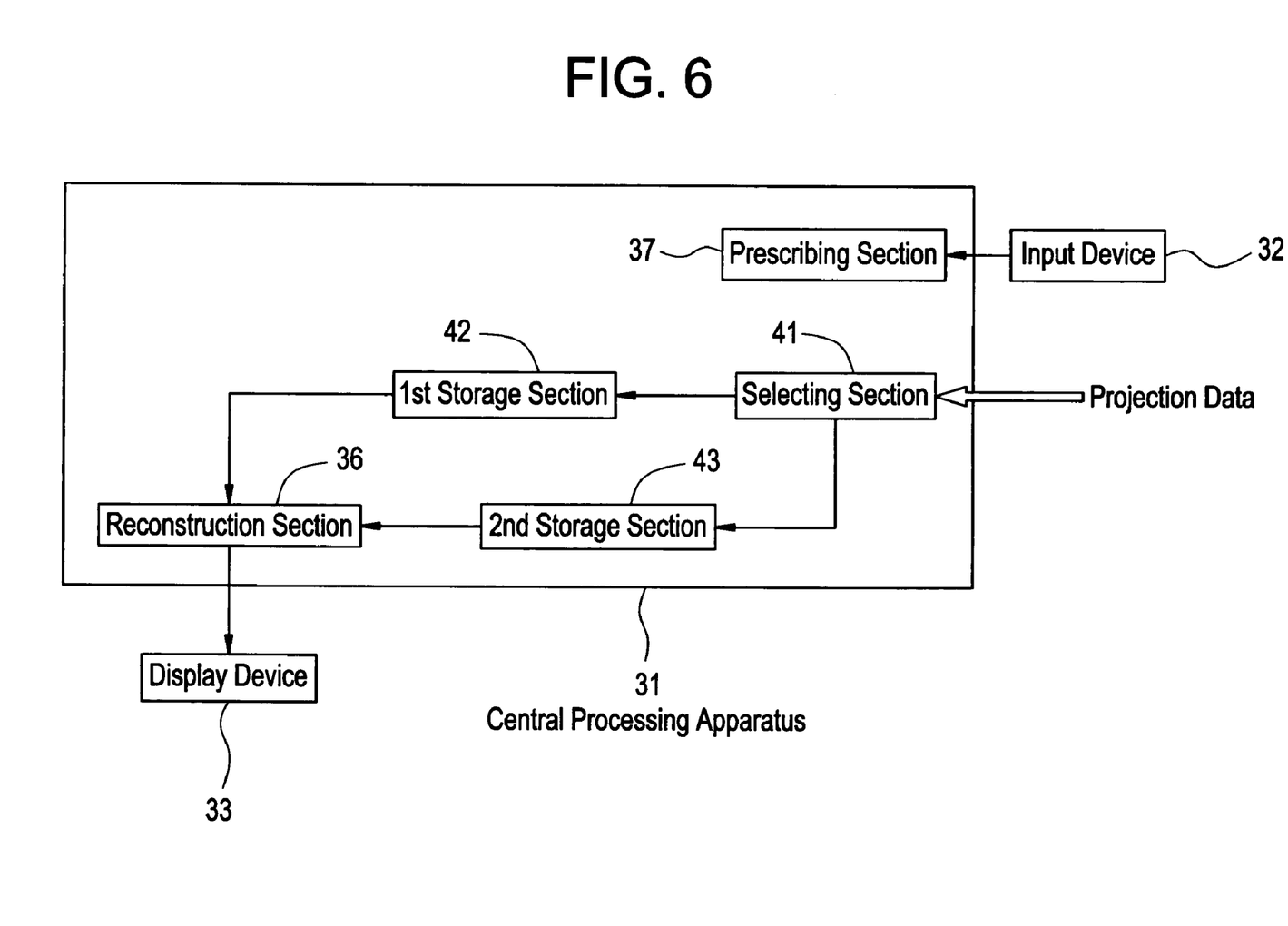
FIG. 6 is a block diagram schematically showing the configuration of the central processing apparatus 31 in accordance with Variation 2.

The central processing apparatus 31 further comprises a second storage section for storing projection data to be reconstructed at a higher priority.

FIG. 6 is a block diagram schematically showing the configuration of the central processing apparatus 31 in accordance with Variation 2.

The central processing apparatus 31 comprises a selecting section 41, a first storage section 42, a second storage section 43, the reconstruction section 36 and prescribing section 37.

The selecting section 41 selects between projection data to be reconstructed at a higher priority and other projection data.

The first storage section 42 stores the other projection data, that is, projection data to be reconstructed in the order of scanning.

The second storage section 43 stores the projection data to be reconstructed at a higher priority.

The reconstruction section 36 reconstructs the projection data stored in the first storage section 42 and second storage section 43.

The prescribing section 37 prescribes a higher-priority position, and defines projection data to be input to the second storage section 43 based on the prescribed higher-priority position.

The central processing apparatus 31 controls the selecting section 41, first storage section 42, second storage section 43 and reconstruction section 36 based on the conditions prescribed at the prescribing section 37.

The scan gantry 2 inputs projection data to the central processing apparatus 31 via the data collecting section 24. The selecting section 41 in the central processing apparatus 31 outputs the projection data to the first storage section 42 or the second storage section 43 based on position information output from the scan gantry 2. The central processing apparatus 31 causes the projection data to be output from the first storage section 42 and second storage section 43 to the reconstruction section 36. At that time, the central processing apparatus 31 outputs the projection data stored in the second storage section 43 to the reconstruction section 36 at a higher priority. For example, if projection data are stored in both the first storage section 42 and second storage section 43, the central processing apparatus 31 outputs the projection data in the second storage section 43 to the reconstruction section 36, and the projection data stored in the first storage section 42 to the storage device 34.

The reconstruction section 36 reconstructs the input projection data to produce an image at the prescribed position or time. The central processing apparatus 31 displays the produced image on the display device 33. By thus selectively storing projection data in the first storage section 42 and second storage section 43, projection data stored in either one of the storage sections can be reconstructed at a higher priority. This variation may be applied to imaging according to Variation 1 in which the scan position is fixed to observe a temporal change of the subject.

According to the radiation tomographic imaging apparatus of the present invention, since the apparatus has a prescribing section for prescribing beforehand the position or time of an image to be reconstructed at a higher priority, an accurate image can be produced at a position or time desired by the user. Moreover, since the reconstruction section interrupts reconstruction processing to prepare for reconstruction of an image at the higher-priority position or higher-priority time before a scan at the prescribed higher-priority position or higher-priority time, reconstruction can be performed following the scan at the desired position or time. Furthermore, since the user can observe an image at a desired position without a lag from a scan, imaging efficiency is improved. The configuration as described above is useful especially when the speed of reconstruction is lower than that of scanning, or when a plurality of images are produced from the same projection data.

According to the imaging method of the present invention, since the position or time of an image to be reconstructed at a higher priority is prescribed beforehand, an accurate image can be produced at a position or time desired by the user. Moreover, since reconstruction processing is interrupted to prepare for reconstruction of an image at the higher-priority position or higher-priority time before a scan at the prescribed higher-priority position or higher-priority time, reconstruction can be performed following the scan at the desired position or time. Furthermore, since the user can observe an image at a desired position without a lag from a scan, imaging efficiency is improved.

The radiation tomographic imaging apparatus and an imaging method using it of the present invention is not limited to these embodiments.

For example, two consecutive image production positions may be selected as the higher-priority positions at which reconstruction is to be made at a higher priority. Moreover, the display layout of the display device shown in FIG. 5 is merely an example, and the number of divided sections or images displayed therein may be appropriately changed.

Many widely different embodiments of the invention may be configured without departing from the spirit and the scope of the present invention. It should be understood that the present invention is not limited to the specific embodiments described in the specification, except as defined in the appended claims.

The invention claimed is:

1. A radiation tomographic imaging apparatus comprising:
   a scanning device for scanning a predefined region in a subject;
   a prescribing device for prescribing beforehand a position at which an image of said subject is to be produced at a higher priority in the scan region in said subject; and
   a reconstructing device for sequentially reconstructing an image of said subject from projection data sequentially obtained by said scanning device,
   wherein once projection data at said prescribed higher priority position has been obtained from said scanning device, said reconstructing device interrupts an ongoing reconstruction and reconstructs an image at said higher priority position before reconstructing any other images, such that a reconstruction order of the image is not dependant on a given scan direction.

2. The radiation tomographic imaging apparatus of claim 1, wherein said scanning device outputs position information on the scan position to said reconstructing device, and said reconstructing device interrupts reconstruction of other projection data before said scanning device conducts a scan at said higher-priority position based on the position information from said scanning device.

3. The radiation tomographic imaging apparatus of claim 1, wherein:
   said reconstructing device reconstructs an image at a position subsequent to said higher-priority position after reconstructing said projection data at said higher-priority position.

4. The radiation tomographic imaging apparatus of claim 1, further comprising:
   a display device for displaying an image of said subject reconstructed by said reconstructing device,
   wherein said display device displays an image at said higher-priority position reconstructed by said reconstructing device until all projection data are obtained by said scanning device.

5. The radiation tomographic imaging apparatus of claim 1, further comprising:
   a display device for displaying an image of said subject reconstructed by said reconstructing device, wherein said display device displays a reconstructed image at said higher-priority position until images from all projection data are reconstructed by said reconstructing device.

6. The radiation tomographic imaging apparatus of claim 1, wherein:
said scanning device comprises a radiation source and a radiation detector disposed to face said radiation source with a subject placed therebetween.

7. The radiation tomographic imaging apparatus of claim 1, wherein:
said scanning device employs X-rays as radiation.

8. A radiation tomographic imaging apparatus comprising:
a scanning device for consecutively scanning a predefined position in a subject;
a prescribing device for prescribing beforehand a time at which obtained projection data is to be reconstructed at a higher priority at the scan position in said subject; and
a reconstructing device for sequentially reconstructing an image of said subject from projection data sequentially obtained by said scanning device,
wherein once said projection data at said prescribed higher-priority time has been obtained from said scanning device, said reconstructing device interrupts an ongoing reconstruction and reconstructs an image of said subject at said higher priority time before reconstructing any other images, such that a reconstruction order of the image is not dependant on a given scan direction.

9. The radiation tomographic imaging apparatus of claim 8, wherein:
said scanning device outputs the scan time to said reconstructing device, and
said reconstructing device interrupts reconstruction of other projection data before said scanning device conducts a scan at said higher-priority time based on said scan time.

10. The radiation tomographic imaging apparatus of claim 8, wherein said reconstructing device reconstructs said projection data obtained following said higher-priority time after reconstructing said projection data at said higher-priority time.

11. The radiation tomographic imaging apparatus of claim 8, further comprising:
a display device for displaying an image of said subject reconstructed by said reconstructing device,
wherein said display device displays an image at said higher-priority time reconstructed by said reconstructing device until all projection data are obtained by said scanning device.

12. The radiation tomographic imaging apparatus of claim 8, further comprising:
a display device for displaying an image of said subject reconstructed by said reconstructing device,
wherein said display device displays a reconstructed image at said higher-priority time until images from all projection data are reconstructed by said reconstructing device.

13. The radiation tomographic imaging apparatus of claim 8, wherein:
said scanning device comprises a radiation source and a radiation detector disposed to face said radiation source with a subject placed therebetween.

14. The radiation tomographic imaging apparatus of claim 8, wherein:
said scanning device employs X-rays as radiation.

15. An imaging method using a radiation tomographic imaging apparatus having a radiation source and a radiation detector disposed to face said radiation source with a subject placed therebetween, said method comprising the steps of:
defining a reference position in said subject placed at a certain position;
prescribing an image production position in said subject at which reconstruction is to be made at a higher priority, based on said reference position;
scanning a predefined region in said subject placed at the certain position while rotating at least one of said radiation source and radiation detector around said subject; and
sequentially reconstructing an image at every image production position based on the projection data sequentially obtained at said step of scanning, wherein said step of scanning and said step of reconstructing run simultaneously, and once said projection data at said higher-priority position has been obtained at said step of scanning, said step of reconstructing interrupts an ongoing reconstruction and reconstructs an image at said higher priority position before reconstructing any other images, such that a reconstruction order of the image is not dependant on a given scan direction.

16. The imaging method of claim 15, further comprising:
a displaying step of displaying an image of said subject reconstructed at said step of reconstructing after said step of reconstructing,
wherein said displaying step displays an image at said higher-priority position reconstructed at said reconstructing step until the scan on said scan region is completed at said step of scanning.

17. The imaging method of claim 15, further comprising:
a displaying step of displaying an image of said subject reconstructed at said step of reconstructing after said step of reconstructing,
wherein said displaying step displays a reconstructed image at said higher-priority position until images from all projection data are reconstructed at said step of reconstructing.

18. The imaging method of claim 15, wherein:
said step of reconstructing performs reconstruction on said projection data at a position subsequent to said higher-priority position after reconstructing said projection data at said higher-priority position.

* * * * *